(12) United States Patent
McCarthy

(10) Patent No.: US 12,312,295 B1
(45) Date of Patent: May 27, 2025

(54) CHEMICAL COMPOUND THAT BINDS TO NERVES WHILE PERMITTING DETECTION VIA COMPUTED TOMOGRAPHY OR X-RAY

(71) Applicant: James Edward McCarthy, Fort Collins, CO (US)

(72) Inventor: James Edward McCarthy, Fort Collins, CO (US)

( * ) Notice: Subject to any disclaimer, the term of this patent is extended or adjusted under 35 U.S.C. 154(b) by 338 days.

(21) Appl. No.: 17/989,489

(22) Filed: Nov. 17, 2022

Related U.S. Application Data

(63) Continuation-in-part of application No. 17/498,603, filed on Oct. 11, 2021.

(51) Int. Cl.
 *C07C 231/02* (2006.01)
(52) U.S. Cl.
 CPC .................................. *C07C 231/02* (2013.01)
(58) Field of Classification Search
 None
 See application file for complete search history.

(56) References Cited

U.S. PATENT DOCUMENTS 6,384,278 B1  5/2002  Tang et al.

OTHER PUBLICATIONS

Hanson, J. Advances in the direct iodination of aromatic compounds. Journal of Chemical Research, 2006; 277-280.
Allen, C., Chhatwal, A., Williams, J. Chem Commun, 2012; 48: 666-668.
Chemical Abstract Service (CAS): 53663-23-3.
Chemical Abstract Service (CAS): 24154-37-8.
Chemical Abstract Service (CAS): 57830-60-1.

*Primary Examiner* — Michael G. Hartley
*Assistant Examiner* — Samantha L Mejias
(74) *Attorney, Agent, or Firm* — Plager Schack LLP; Mark H. Plager; Kara K. Verryt

(57) ABSTRACT

A chemical compound that binds to nerves and provides for visualization of the nerves using computed tomography or x-ray may include at least two iodo groups bonded to a local anesthetic with an aromatic functional group/benzene ring, wherein the local anesthetic is capable of binding to a nerve. The chemical compound may have the chemical structure $C_6H_2I_xR$, wherein x is 2 or 3; R is an amino group or $NHR^1$; and $R^1$ is an amide group, such as $-CON(CH_2CH_3)_2$.

1 Claim, 2 Drawing Sheets

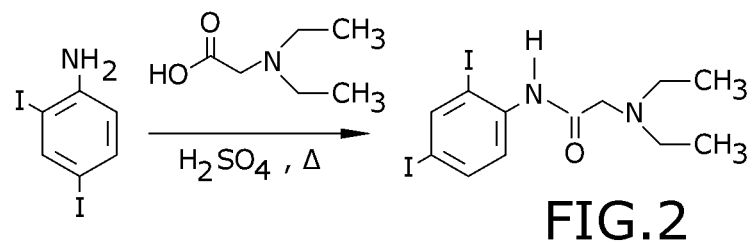
FIG.2
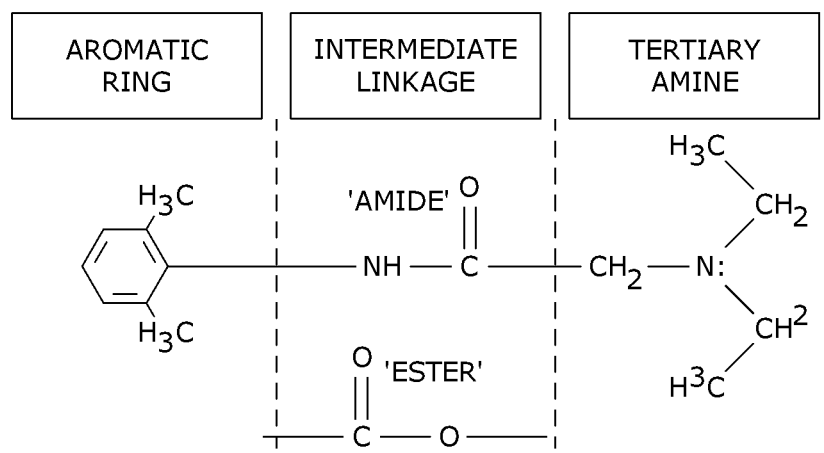
FIG.3
(PRIOR ART)
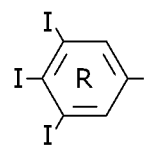 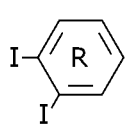 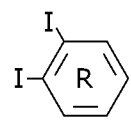
FIG.4  FIG.5  FIG.6

CHEMICAL COMPOUND THAT BINDS TO NERVES WHILE PERMITTING DETECTION VIA COMPUTED TOMOGRAPHY OR X-RAY

RELATED APPLICATION

This application claims priority to and is a continuation-in-part application of U.S. Ser. No. 17/498,603 filed on Oct. 11, 2021, the entire contents of which is herein incorporated by reference.

BACKGROUND

The embodiments described herein relate generally to chemical compounds and, more particularly, to a radio opaque chemical compound designed to bind to nerves, such as peripheral nerves, for imaging purposes.

Existing technologies and methods do not permit high resolution visualization of neurons in living mammals due to: (i) the lack of a sodium channel neuron-specific contrast agent, (ii) the toxicity of neuron-specific contrast agents that are currently used in terminal animals, (iii) the lack of imaging resolution with ionizing radiation (etc., computed tomography ("CT") or x-ray), and (iv) motion artifact. As such, there is currently no known method of imaging the human nervous system in vivo with a contrast agent to permit visualization using computed tomography or x-ray.

Lidocaine is a synthetic aminoethylamide with local anesthetic properties. It functions by stabilizing the neuronal membrane by binding to and inhibiting voltage-gated sodium channels within the nervous system, including the peripheral nervous system, thereby inhibiting the ionic fluxes required for the initiation and conduction of impulses and effecting local anesthesia. Lidocaine is the monocarboxylic acid amide resulting from the formal condensation of N,N-diethylglycine with 2,6-dimethylaniline.

Lidocaine, which is used herein as a base model for which a nerve contrast agent is modeled after, has been preceded by a host of local anesthetics over the last 150 years, each of which may also serve to provide delivery of a contrast agent to the peripheral nervous system for imaging using ionizing radiation. Examples of these agents include cocaine, benzocaine, eucaine, procaine, and tetracaine. Developed in the years following lidocaine, chloroprocaine incorporates a halogen (chlorine) within the aromatic ring, suggesting that other halogens, such as iodine, may also be bound to one of the functional groups within the molecule and still bind to the sodium-ion channel.

Therefore, what is needed is a molecule that specifically binds to human nerves and provides contrast enhancement using computed tomography or x-ray, wherein the molecule is non-toxic at therapeutic concentrations.

SUMMARY

Some embodiments of the present disclosure include a chemical compound that binds to nerves and provides for visualization of the nerves using computed tomography or x-ray. The chemical compound may include at least two iodo groups bonded to a local anesthetic with an aromatic functional group/benzene ring, wherein the local anesthetic is capable of binding to a nerve. The chemical compound may have the chemical structure $C_6H_2I_xR$, wherein x is 2 or 3; R is an amino group or $NHR^1$; and $R^1$ is an amide group, such as $-CON(CH_2CH_3)_2$. Thus, the chemical compound may be a diiodo or triiodo local anesthetic derivative.

BRIEF DESCRIPTION OF THE FIGURES

The detailed description of some embodiments of the invention is made below with reference to the accompanying figures, wherein like numerals represent corresponding parts of the figures.

FIG. 2 is a schematic diagram showing a synthesis reaction that results in one embodiment of the present disclosure.

FIG. 3 is a schematic diagram showing the chemical structure of conventional local anesthetics.

FIG. 4 is schematic diagram of one embodiment of the present disclosure.

FIG. 5 is a schematic diagram of one embodiment of the present disclosure.

FIG. 6 is a schematic diagram of one embodiment of the present disclosure.

DETAILED DESCRIPTION

Figure 1A:
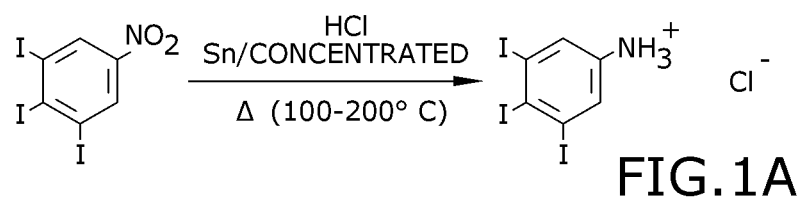
FIG. 1A-1C are schematic diagrams showing synthesis reactions that result in one embodiment of the present disclosure.

In the following detailed description of the invention, numerous details, examples, and embodiments of the invention are described. However, it will be clear and apparent to one skilled in the art that the invention is not limited to the embodiments set forth and that the invention can be adapted for any of several applications.

The composition of the present disclosure may be used as a compound that binds to nerves to provide for tomography imaging of the nerves and may comprise the following elements. This list of possible constituent elements is intended to be exemplary only, and it is not intended that this list be used to limit the composition of the present application to just these elements. Persons having ordinary skill in the art relevant to the present disclosure may understand there to be equivalent elements that may be substituted within the present disclosure without changing the essential function or operation of the composition.

The various elements of the present disclosure may be related in the following exemplary fashion. It is not intended to limit the scope or nature of the relationships between the various elements and the following examples are presented as illustrative examples only.

As used herein, the term "room temperature" may refer to a temperature of from about 20 to about 22° C.

By way of example, and referring to the Figures, some embodiments of the present disclosure include a chemical compound that binds to nerves to provide contrast enhancement of the nervous system to permit detection, such as visualization or visual detection, wherein the composition is non-toxic at therapeutic concentrations, the chemical compound comprising a triiodo- or diiodo-local anesthetic derivative.

More specifically, the compound may be designed to bind to nerves and may provide for imaging of the nerves using computed tomography, wherein the compound may comprise at least two iodo groups, such as two or three iodo groups, bonded to a local anesthetic with an aromatic functional group/benzene ring, wherein the local anesthetic is capable of binding to a nerve. As shown in FIG. 3, a local anesthetic conventionally comprises three basic parts: a hydrophobic aromatic ring, an intermediate chain, and a hydrophilic part. In embodiments, the intermediate chain may comprise, for example, an amide or an ester. In a particular example, the local anesthetic may comprise procaine or lidocaine. The chemical compound of the present disclosure may retain the three critical elements of a local anesthetic: the hydrophobic aromatic ring with the addition of two or three iodine groups (as shown in FIGS. 4-6), the intermediate chain, such as one that is a ketone identical to that in lidocaine, and the hydrophilic component, such as that being similar to the diethylglycine moiety in lidocaine.

As mentioned above, the chemical compound of the present disclosure may be a local anesthetic derivative including two or three diiodo groups and, thus, the chemical formula of the chemical compound may be $C_6H_2I_xR$, wherein x is 2 or 3 and R may be an amino group or $NHR^1$, wherein $R^1$ may comprise an amide group, such as —CON $(CH_2CH_3)_2$. Thus, the chemical compound may be 2-(Diethylamino)-N-(1,2,3-triiodophenyl)acetamide or 2-(Diethylamino)-N-(1,3-diiodophenyl)acetamide.

In a first embodiment, the chemical compound may be a triiodo local anesthetic derivative with the following chemical formula (as shown in FIG. 4): $C_6H_2I_3R$, wherein R may be an amino group or $NHR^1$, wherein $R^1$ may comprise an amide group, such as —$CON(CH_2CH_3)_2$. Thus, the chemical compound may be 2-(Diethylamino)-N-(1,2,3-triiodophenyl)acetamide having the structure shown in the product of FIG. 1C.

In a second embodiment, the chemical compound of the present disclosure may be a diiodo local anesthetic derivative with the following chemical formula (as shown in FIGS. 5 and 6): $C_6H_3I_2R$, wherein R may be an amino group of $NHR^1$, wherein $R^1$ may comprise an amide group, such as —$CON(CH_2CH_3)_2$. In a particular embodiment, the chemical compound may be 2-(Diethylamino)-N-(1,3-diiodophenyl)acetamide and may have the structure shown in FIG. 2.

Figure 1B:
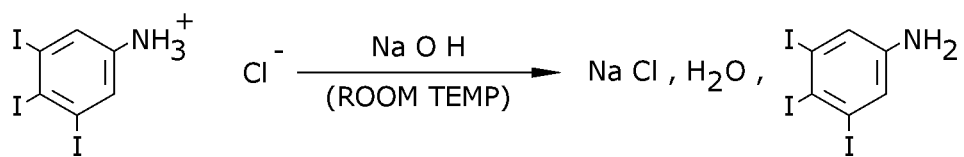
Figure 1C:
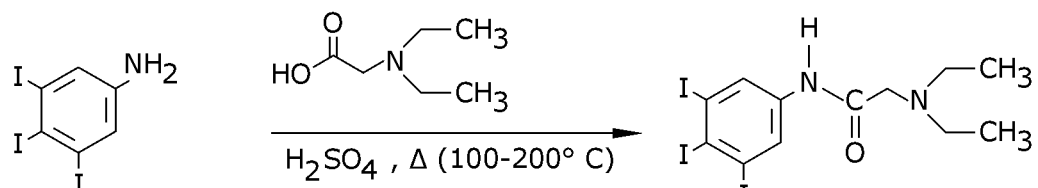

In a particular embodiment, such as that shown in FIGS. 1A-1C, synthesizing an embodiment of the triiodo local anesthetic derivative of the present disclosure may comprise following the steps shown in FIGS. 1A-1C. More specifically, 1,2,3-triiodo-5-nitrobenzene, which has the unique chemical identification number provided through Chemical Abstract Service (CAS): 53663-23-3, which is herein incorporated by reference in its entirety. 1,2,3-triiodo-5-nitrobenzene is manufactured by a number of companies and is readily available. To minimize the number of reactions required in one setting, it may be desirable to begin the synthesis of the compound of the present disclosure with the commercially available product, though the synthesis of the 1,2,3-triiodo-5-nitrobenzene may be produced by first selecting an iodine containing compound, such as $HICl_2$, $NaICl_2$, $KIC_{12}$, or ICl; and reacting nitrobenzene with the iodine containing compound (which may preferably be $NaICl_2$) in a 1:1 stoichiometric relationship by adding the iodinating compound over a four hour time period at a temperature of from about 40 to about 70° C. Details regarding such reactions may be found in Hanson, J., *Advances in the direct iodination of aromatic compounds*, Journal of Chemical Research, 2006; 277-280, which is herein incorporated by reference.

Following the iodination of nitrobenzene, the nitro group may then be reduced via metallic tin and hydrochloric acid under heat, for example at a temperature of at least about 100° C., to generate 1,2,3-triiodophenylammonium using a reflux condenser, as shown in FIG. 1A. The 1,2,3-triiodophenylammonium may then be collected in a liquid form using a reflux condensation apparatus for the next reaction. The 1,2,3-triiodophenylammonium may then be oxidized using NaOH or another common oxidizing agent, such as LiOH or KOH at room temperature, as shown in FIG. 1B, to generate 1,2,3-triiodoaniline. Amidation of the 1,2,3-triiodoaniline may then be accomplished through several well-known amidation reactions with the production of one equivalent of water. It is to be noted that reactions of carboxylic acid (N,N-diethylglycine in this example) and amine groups (contained within the 1,2,3-triiodo-5-nitrobenzene molecule in this example) are challenging in a one-step container due to competing acid-base reactions, and thus may require conversion of the carboxylic acid to the corresponding acid chloride (using the Schotten-Baumann reaction) before reacting the amine group to potentiate amidation.

In one example of amidation for the purposes of the present disclosure, N,N-diethylglycine may be added in a 1:1 molar ratio with 1,2,3-triiodo-5-bitrobenzene in the presence of concentrated sulfuric acid under heat, such as at a temperature of from about 100 to about 200° C., and preferable at about 150° C., over 2-10 hours to afford the final triiodo anesthetic derivative contrast agent, as shown in FIG. 1C. The carboxamide, 2-(Diethylamino)-N-(1,2,3-triiodophenyl)acetamide, may be purified by any suitable purification method known in the art. For example, the carboxamide may be purified by recrystallization or by fractionation on one or more solid chromatographic supports, alone or linked in tandem. Suitable recrystallization solvent systems include, but are not limited to, acetonitrile, methanol, and tetrahydrofuran.

In another embodiment, the amidation reaction between N,N-diethylglycine and 1,2,3-triiodo-5-nitrobenzene may be brought about by thermal amidation without a catalyst using temperatures greater than about 110° C. for prolonged period of times, such as at least about 24 hours, in a 1:1 molar ratio to yield 2-(diethylamino)-N-(1,2,3-triiodophenyl)acetamide. Details regarding thermal amidation may be found in Allen, C. et al., *J. Chem Commun*, 2012; 48: 666-668, which is herein incorporated by reference.

In a further example, amidation using the aforementioned amine and carboxylic acids pertaining to the present disclosure may including using a one-step process in the presence of a boron containing compound (e.g., boric acid) and a chelating agent (e.g., 2-pyridinylamine) whereby 1:1 molar ratios of the reactants and the molar ratio of the boron containing compound to 2-pyridinylamine is preferably about 1:1. Details regarding this type of amidation reaction may be found in U.S. Pat. No. 6,384,278 to Tang et al, which is herein incorporated by reference in its entirety. The molar ratio of the boron containing compound or 2-pyridinylamine to the aromatic amine or acid preferably ranges from about 1:50 to about 1:4. The reaction mixture may contain about 0.1 to about 4 moles of 1,2,3-triiodo-5-nitrobenzene, from about 0.1 to about 4 moles of N,N-diethylglycine, and from about 0.001 to about 4 moles of the boron containing compound per liter of reaction mixture. The reaction mixture may also optionally include from about 0.001 moles to about 8 moles of 2-pyridinylamine per liter of reaction mixture. The reaction may be performed by refluxing a mixture of 1,2,3-Triiodo-5-Nitrobenzene and N,N-diethylglycine in toluene and in the presence of the boron containing compound and 2-pyridinylamine at a temperature of about 110° C. and refluxed for about 1 to about 16 hours.

In another embodiment, generating the triiodo anesthetic nerve contrast of the present disclosure may comprise beginning with 2,4,6-Triiodoaniline, Chemical Abstract Service (CAS): 24154-37-8, which is herein incorporated by reference in its entirety. This approach may bypass the reduction of the nitrate group, as mentioned previously, and again contains an aromatic amine group, which may be combined through amidation to N,N-diethylglycine using any of the reactions previously described to create the final functional compound used for a peripheral nerve contrast: 2-(Diethylamine)-N-(2,4,6-triiodophenyl)acetamide.

As shown in FIG. 2, synthesizing an embodiment of the diiodo local anesthetic derivative of the present disclosure may comprise condensing N,N-diethylglycine with diiodo aniline and sulfuric acid under heat to afford the final diiodo anesthetic derivative. Similar to the triiodo product, the di-iodo synthesis may begin with a commercially available product, 1,3-diiodo-nitrobenzene, which has the unique chemical identification number provided through Chemical Abstract Service (CAS): 57830-60-1, which is herein incorporated by reference in its entirety. The nitro group within the benzene ring may be reduced via reduction with metallic tin and hydrochloric acid under heat at a temperature of, for example, about 100° C., to generate 1,3-diiodophenylamonium using a reflux condenser. The 1,3-diiodophenylamonium may then be collected in a liquid form for the next reaction. The 1,3-diphenylamonium may then be oxidized using NaOH or other common oxidizing agents, such as LiGH or KOH, at room temperature to generate 1,3-diiodoaniline. Condensing N,N-diethylglycine with the diiodoaniline may be accomplished by the addition of concentrated sulfuric acid under heat, such as at a temperature of from about 100 to about 200° C. and preferably at about 150° C., over 2 to 10 hours to afford the final diiodo anesthetic derivation, 2-(diethylamino)-N-(1,3-diiodophenyl)acetamide. The carboxamide may be purified using any conventional purification methods, as previously described.

Providing contrast enhancement of human nerves using computed tomography or x-ray may comprise delivering, to a patient in need, a therapeutically effective dosage of the chemical compound of the present disclosure. Such indications may include, but are not limited to, identification of peripheral sensory nerves to the articular surface for the purposes of destruction for the alleviation of joint pain, surgical navigation to protect critical nerves, such as the facial, recurrent laryngeal, or peripheral nerves within the brachial plexus, diagnostic radiology of peripheral nerve disorders, and basic science evaluation of peripheral nerve physiology. Delivery of the compound may be achieved by placing the compound into a syringe and injecting the chemical into a vein, subcutaneous tissues, or peripheral tissue surrounding the nerve to be imaged. More specifically, delivering the composition to the patient may be done numerous ways, including injecting the compound into the veins of an extremity after exsanguinating the limb and applying a tourniquet (e.g., Bier block technique). When the limb is exsanguinated, the tourniquet may be inflated, and then the chemical solution may be injected into the limb. The tourniquet may then be slowly deflated after the compound as had time to bind to the sodium gated ion channel (e.g., NaV 1.6 or NaV 1.7), and the limb may be imaged using CT or x-ray after the chemical has been evacuated from the interstitial space.

Alternatively, the injection of the compound may occur immediately around the nerve, wherein, after waiting a sufficient period of time for the chemical to bind to its receptor within the nerve and then be evacuated from the interstitial space, the nerve may be imaged using CT or x-ray.

Using the chemical compound of the present disclosure in the above-described manner may provide for viewing of a targeted nerve with contrast. A conventional display screen may provide imaging showing the patient having nerves, wherein at least one nerve includes contrast.

While the above descriptions indicate that the compound includes a triiodo or diiodo group added to lidocaine, which is a specific local anesthetic, the compound may, instead, include a triiodo or diiodo group bonded to any specific local anesthetic that binds to nerves and includes an aromatic functional group/benzene ring.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

The invention claimed is:

1. A method for imaging nerves using computed tomography or x-ray, the method comprising: administering, to a patient in need, a therapeutically effective dosage of a compound that binds to the nerves and provides for imaging of the nerves, wherein the compound is selected from

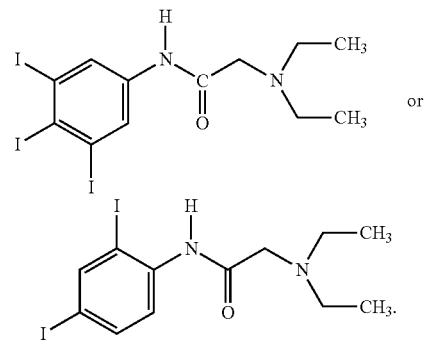

* * * * *